United States Patent
Dutta et al.

(10) Patent No.: US 7,694,547 B2
(45) Date of Patent: Apr. 13, 2010

(54) ROBUST HIGH TEMPERATURE COMPOSITE AND CO SENSOR MADE FROM SUCH COMPOSITE

(75) Inventors: Prabir K. Dutta, Worthington, OH (US); Ramamoorthy Ramasamy, Strongsville, OH (US); Xiaogan Li, Columbus, OH (US); Sheikh A. Akbar, Hilliard, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 15 days.

(21) Appl. No.: 12/040,597

(22) Filed: Feb. 29, 2008

(65) Prior Publication Data

US 2008/0209982 A1 Sep. 4, 2008

Related U.S. Application Data

(60) Provisional application No. 60/904,450, filed on Mar. 1, 2007.

(51) Int. Cl.
*G01N 27/04* (2006.01)
(52) U.S. Cl. ...................................................... 73/23.2
(58) Field of Classification Search ................... 73/23.2
See application file for complete search history.

(56) References Cited

U.S. PATENT DOCUMENTS

| | | | | |
|---|---|---|---|---|
| 4,732,738 A | * | 3/1988 | Nakatani et al. | 422/94 |
| 5,248,617 A | * | 9/1993 | De Haan | 436/137 |

(Continued)

FOREIGN PATENT DOCUMENTS

DE 19701493 C1 6/1998

OTHER PUBLICATIONS

M.C. Carotta, M. Ferroni, D. Gnani, V. Guidi, M. Merli, G. Martinelli, M.C. Casale, M. Notaro; Nanostructured pure and Nb-doped TiO2 as thick film gas sensors for environmental monitoring; Elsevier Science S.A., Sensors and Actuators B 58, pp. 310-317; received Sep. 15, 1998; accepted Feb. 8, 1999; copyright 1999; Italy.

(Continued)

*Primary Examiner*—Hezron Williams
*Assistant Examiner*—Rodney T Frank
(74) *Attorney, Agent, or Firm*—Calfee, Halter & Griswold LLP

(57) ABSTRACT

Described herein is a composite exhibiting a change in electrical resistance proportional to the concentration of a reducing gas present in a gas mixture, detector and sensor devices comprising the composite, a method for making the composite and for making devices comprising the composite, and a process for detecting and measuring a reducing gas in an atmosphere. In particular, the reducing gas may be carbon monoxide and the composite may comprise rutile-phase $TiO_2$ particles and platinum nanoclusters. The composite, upon exposure to a gas mixture containing CO in concentrations of up to 10,000 ppm, exhibits an electrical resistance proportional to the concentration of the CO present. The composite is useful for making sensitive, low drift, fast recovering detectors and sensors, and for measuring CO concentrations in a gas mixture present at levels from sub-ppm up to 10,000 ppm. The composites, and devices made from the composites, are stable and operable in a temperature range of from about 450° C. to about 700° C., such as may be found in a combustion chamber.

17 Claims, 5 Drawing Sheets

U.S. PATENT DOCUMENTS

| | | | | |
|---|---|---|---|---|
| 5,457,333 | A | * | 10/1995 | Fukui ........................ 257/253 |
| 5,629,474 | A | * | 5/1997 | Williams .................... 73/23.2 |
| 5,814,281 | A | * | 9/1998 | Williams et al. .............. 422/88 |
| 6,202,471 | B1 | * | 3/2001 | Yadav et al. ............... 73/31.05 |
| 6,513,362 | B1 | * | 2/2003 | Yadav et al. ............... 73/31.05 |
| 6,660,231 | B2 | * | 12/2003 | Moseley ...................... 422/98 |
| 6,813,931 | B2 | * | 11/2004 | Yadav et al. ............... 73/31.05 |
| 2005/0045477 | A1 | * | 3/2005 | Wei et al. .................... 204/431 |

OTHER PUBLICATIONS

Rajnish K. Sharma, M.C. Bhatnagar; Improvement of the oxygen gas sensitivity in doped $TiO_2$ thick films; Elsevier Science S.A., Sensors and Actuators B 56, pp. 215-219; received Aug. 19, 1998; accepted Dec. 3, 1998; copyright 1999; India.

Akio Takami; Development of Titania Heated Exhaust-Gas Oxygen Sensor; Ceramic Bulletin, vol. 67, No. 12, 1988, pp. 1956-1960; Japan.

Louis D. Rampino, F.F. Nord; Preparation of Palladium and Platinum Synthetic High Polymer Catalysts and the Relationship between Particle Size and Rate of Hydrogenation; Contribution from the Department of Organic Chemistry, Fordham University, Palladium and Platinum Synthetic High Polymer Catalysts, vol. 63, pp. 2745-2749; Oct. 1941; New York, NY, USA.

* cited by examiner (3a)

(3b)

(4a)

(4b)

(5a)

(5b)

ROBUST HIGH TEMPERATURE COMPOSITE AND CO SENSOR MADE FROM SUCH COMPOSITE

CROSS-REFERENCE TO RELATED APPLICATIONS

The present application claims priority to, and any other benefit of, U.S. Provisional Patent Application Ser. No. 60/904,450 filed Mar. 1, 2007, and entitled ROBUST HIGH TEMPERATURE SEMICONDUCTING CO SENSOR the entire contents of which is hereby incorporated by reference.

STATEMENT ON FEDERALLY FUNDED RESEARCH

This invention was funded at least in part by The Department of Energy grant number DE-PS26-02NT41422. The government may have certain rights in this invention.

BACKGROUND

In many industries there is much interest in monitoring carbon monoxide (CO) levels during industrial processes, specifically when balancing ratios of oxygen ($O_2$) to fuel during combustion. When unable to monitor CO levels manufacturers tend to run lean in order to avoid explosions. However, this results in engine knocking and can lead to formation of $NO_x$ species. By monitoring CO levels an ideal balance of $O_2$ to fuel may be maintained, thus avoiding knocks and minimizing pollution. Existing gas sensors are made from metal oxide-based materials that usually are not selective but rather will respond indiscriminately to a broad spectrum of reactive gases. In addition to an indiscriminate response, state of the art detectors and sensors made from such metal oxide-based materials will often exhibit unstable baseline resistance, continuous drift, and poor recovery time.

There is a need for new materials that exhibit selective changes in their properties in the presence of CO or other hydrocarbon gases and that respond selectively to CO, and for new low drift detector and sensor devices made from such materials that also respond selectively to gases such as CO or other hydrocarbon gases. Additionally, a need exists for materials, detector and sensor devices, and methods employing these devices for CO detection and measurement that are more economical than the current materials and methods used to detect and measuring CO. Currently, there is a need for new solid state CO sensors useful for optimizing fuel efficiency in a variety of industrial processes and a need for new materials useful for making CO sensors that can be used to measure local CO concentrations in combustion chambers or in other hostile industrial environments where temperatures between 450-700° C. are reached. Sensors for use in these hostile environments should be able to detect and measure CO present at concentrations as low as sub-ppm level. Sensors for use in these hostile environments should also exhibit minimal drift and quick recovery times.

SUMMARY

Described herein is a composite, devices made from a composite, methods for making a composite, and methods for making devices from a composite that exhibits a change in electrical resistance proportional to the concentration of a reducing gas present in a gas mixture. Also described herein is a process for measuring carbon monoxide (CO) in a gas mixture using the devices made from the composite. In certain exemplary embodiments the reducing gas is carbon monoxide (CO) and the composite comprises rutile-phase $TiO_2$ particles and platinum nanoclusters. Upon exposure to a gas mixture containing oxygen ($O_2$) and CO, the composite exhibits a change in electrical resistance which is proportional to the concentration of CO present in the gas mixture when CO is present in concentrations of from about 0 ppm to 10,000 ppm. The composite is useful for making sensitive, low-drift, fast-recovering CO detectors and sensors for measuring the level of CO present in gas mixtures in concentration ranges from sub-ppm to ppm levels. The composite and any detector or sensor made from the composite is stable and operable at high temperatures, that is at temperature ranging from about 450° C. to about 700° C. Such temperatures may be found, for example, in combustion chambers.

Provided herein is a composite comprising metal oxide particles and metal nanoclusters. The composite when exposed to a gas mixture containing a reducing gas, exhibits an electrical resistance which is proportional to the concentration of the reducing gas present in the gas mixture. An exemplary embodiment is a composite comprising rutile-phase $TiO_2$ particles and platinum nanoclusters, wherein the composite when exposed to a gas mixture containing CO exhibits a change in electrical resistance that is proportional to the concentration of CO present in the gas mixture.

Also provided herein is a device comprising a pair of spaced electrodes operatively connected to a composite comprising metal oxide particles and metal nanoclusters, wherein the composite when exposed to a gas mixture containing a reducing gas exhibits a change in electrical resistance that is proportional to the concentration of the reducing gas present in the gas mixture. In certain exemplary embodiments the device is a CO detector capable of selectively detecting CO in a gas mixture. In other exemplary embodiments the device is a CO sensor capable of measuring the level of CO present in a gas mixture. In other exemplary embodiments the device is a CO sensor capable of measuring the level of CO present in a gas mixture when carbon monoxide is present in the gas mixture at concentrations of up to 10,000 ppm.

Also provided herein is a process for measuring CO in a gas mixture comprising: operatively connecting a pair of spaced electrodes to a composite, the composite comprising rutile-phase $TiO_2$ particles and platinum nanoclusters, wherein the composite when exposed to a gas mixture containing CO exhibits a change in electrical resistance which is proportional to the concentration of CO present in the gas mixture; exposing the composite to a gas mixture containing CO; and measuring the electrical resistance of the composite across the electrodes, while the composite is maintained at a temperature of at least 450° C.

Also provided herein is a method for making a carbon monoxide sensor device comprising sintering a mass of $TiO_2$ particles, impregnating the sintered mass with a dispersion of platinum nanoclusters, curing the impregnated sintered mass to form a porous matrix and operatively connecting the porous matrix to a pair of spaced electrodes to form the sensor.

Also provided herein is a method for making a carbon monoxide sensor device comprising: applying a paste of $TiO_2$ particles onto a substrate having a set of interdigitated electrodes printed on the surface of the substrate which is in physical contact with the paste; sintering the paste to form a porous film of rutile-phase $TiO_2$ on the substrate and operatively connected to the set of interdigitated electrodes; impregnating the porous film with a dispersion comprising: platinum nanoclusters, and polyvinyl alcohol; curing the impregnated film to form the sensor device.

DETAILED DESCRIPTION

Figure 1:
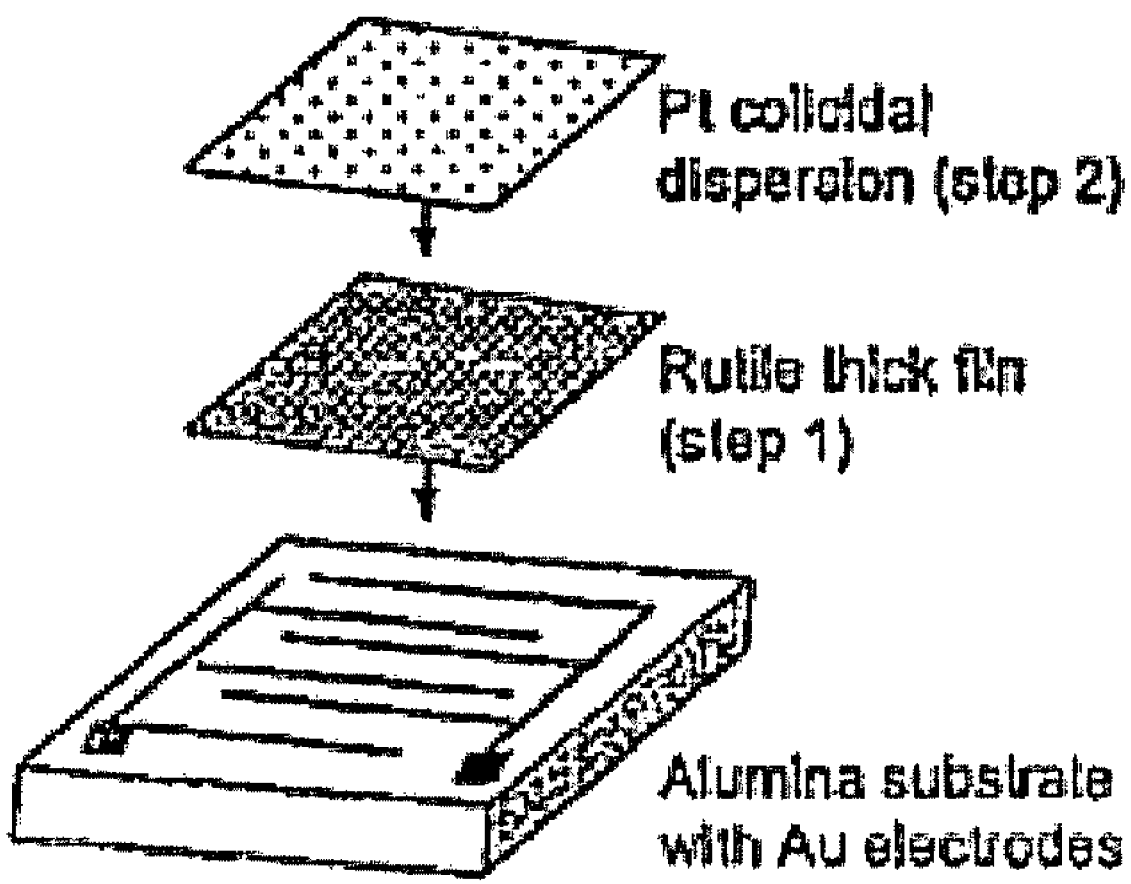
FIG. 1 is an illustration of the steps associated with CO sensor formation.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated (e.g., by use of the term "precisely"), all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations; the numerical values set forth in the specific examples are reported with relative precision. Any numerical values, however, inherently contain certain errors necessarily resulting from error found in their respective measurements.

General

Herein the "electrical resistance" measures how strongly a material opposes the flow of electric current. The unit for measuring electrical resistance (R) is the ohm. A material has a resistance of one ohm when a current of one ampere is produced by a potential of one volt applied across the material.

Herein "operability" as applied to any detector or sensor device means the device is functional and is capable of operating.

Herein "reducing gas" means a gas or volatile compound in a gaseous state which can react with or be oxidized by oxygen ($O_2$) and/or other oxidizing reagents present in either the gas mixture or that are adsorbed onto the surface of the composition herein described.

Herein the "response time" as applied to a detector or sensor device is the time delay between the actual time a reducing gas (i.e. carbon monoxide) is introduced into a gas mixture and the time the device detects the reducing gas in the gas mixture.

Herein the "recovery time" as applied to a detector or sensor device is the time delay between the actual time a reductive gas (i.e. carbon monoxide) is removed from a gas mixture and the time the device indicates the reducing gas is not present in gas mixture.

Herein "selectively detecting" as applied to a detector means that a specific gas can be detected in a gas mixture containing the specific gas, oxygen, and at least one gas other than the specific gas.

Composites and Devices

Provided herein are stable, reproducible, low cost and high temperature detector and sensor devices based on a composite comprising metal oxide particles and metal nanoclusters. The composite, when exposed to a gas mixture containing a reducing gas, exhibits an electrical resistance which is proportional to the concentration of the reducing gas present in the gas mixture. The composite, as well as the detector and sensor devices made from the composite described, exhibit excellent characteristics including desirable response and recovery times.

An exemplary embodiment of a composite comprises rutile-phase $TiO_2$ particles and platinum nanoclusters. The composite, when exposed to a gas mixture containing carbon monoxide (CO), exhibits an electrical resistance which is proportional to the concentration of CO present in the gas mixture. An aspect of the invention is to provide robust, reproducible, stable and fast responding CO sensors operating in a temperature range of from about 450-700° C., which are able to measure levels of CO in concentrations ranging from sub-ppm levels to levels of about 10,000 ppm.

Other exemplary embodiments described herein are modified, low drift Pt—$TiO_2$ CO detectors and sensors. The Pt—$TiO_2$ CO detectors and sensors are operable at elevated temperatures and in hostile industrial environments, such as are found in combustion chambers. The detectors and sensors are useful for optimizing fuel efficiency, in such industries as the power and combustion industries. Advantageously, one example contemplated is a Pt—$TiO_2$ CO sensor that allows for measurement of local CO levels in a combustion chamber in an economical way. The exemplary Pt—$TiO_2$ CO sensor contemplated is operable at temperatures of between 450° C. and 700° C. Furthermore, the CO detectors and sensors contemplated exhibit stable and reproducible properties.

The metal oxide particles and the metal nanoclusters of the composite together provide a surface where various gases present in a gas mixture surrounding the composite can adsorb. The nature of both the particles and nanoclusters and the surface area provided by their size and shape are conducive to adsorption/desorption of many different gases present in the gas mixture. Therefore, interactions between gases in the gas mixture may be promoted by the surfaces of the metal oxide particles and the metal nanoclusters.

Without intending to be bound in theory, it is believed that when both oxygen and CO are present in a gas mixture, either one or both gases may adsorb, at least temporarily, onto a metal oxide particle surface. The CO and $O_2$ gases interact and CO is converted into $CO_2$. The change occurring on the metal oxide particle surface, due to the dynamics of gas adsorption/desorption, impacts the electrical resistance exhibited by the metal oxide particles and consequently the composite. Suitable metal oxides include, for example, but are not limited to metal oxides selected from the group consisting of gallium oxide, tin oxide, titania, zinc oxide, indium oxide and combinations thereof. For certain exemplary embodiments the metal oxide is rutile-phase $TiO_2$.

As mentioned, the various particle and nanocluster surfaces may promote interactions between gases in the mixture. A particle's surface area depends upon both its size and shape. Generally, at equivalent masses of a particulate material, smaller particles have more surface area than larger particles. It is desirable for many applications the detectors and sensors herein described operate reliably at high temperatures. Consequently, the composite structure the devices are built from should be stable at elevated temperatures. Thus, the metal oxide particles and metal nanoclusters used in forming the composite should also be stable at the high operating temperatures. To design a thermally stable particulate-based system, factors that are considered include the thermodynamically favored phases for the different types of materials used and the size of the particulates used.

To produce thermally stable metal oxide particles, the thermodynamic phase and the size and shape of the particles is balanced to provide a high surface area while also maintaining thermal stability. Metal oxide particles suitable for use in forming the composite herein describe have a diameter of from about 0.1 μm to about 20 μm. In some embodiments the metal oxide particles have a diameter of from about 0.5 μm to about 10 μm, in other embodiments the metal oxide particles have a diameter of from about 1 μm to about 5 μm. For certain exemplary embodiments the metal oxide particles are rutile-phase $TiO_2$ particles, in other exemplary embodiments they are rutile-phase $TiO_2$ particles having a diameter of from about 1 μm to about 5 μm.

As with the metal oxide particles, the type of metal, the phase, and the size of the nanoclusters present can impact both the gas adsorption/desorption dynamics occurring in the composite (as well as the resultant electrical resistance) and the thermal stability of the composite. Therefore, the size and type of metal nanoclusters used is balanced to provide both high surface area and suitable thermal stability so that the devices and sensors made from a composite containing the nanoparticles operate reliably and are stable at high temperatures. Metal nanoclusters suitable for use in the composite include, for example, but are not limited to, nanoclusters selected from Pt, Pd, Rh, Ru, Au, Ag, and Cu nanoclusters. Other suitable metal nanoclusters include Ni—Au alloy, Cu—Au alloy, Co—Au alloy, and Ru—Sn alloy nanoclusters. Other suitable metal nanoclusters can be made from copper oxide, copper-cerium oxides, copper-manganese oxides, and catalysts such as ruthenium oxide, $CuMn_2O_4$ (hopcalite), and $CuCoAgMnO_x$ mixed oxides. For certain exemplary embodiments, the metal nanoclusters are platinum nanoclusters. Suitable metal nanoclusters have a diameter of from about of from about 1 nm to about 500 nm, or from about 10 nm to about 100 nm. For certain exemplary embodiments, the nanoclusters are platinum nanoclusters with a diameter of from about 10 nm to about 100 nm.

Where the metal nanoclusters are located within the composite structure (specifically with respect to the metal oxide particles) also influences the resulting properties the composite exhibits, and the subsequent performance any detector or sensor made from the composite has. In some embodiments, the composite is a porous matrix comprising a scaffolding of metal oxide particles and the metal nanoclusters reside in the interstices of this porous matrix in between the metal oxide particles. In other embodiments, the metal nanoclusters are carried on the surface of the metal oxide particles. For certain exemplary embodiments, the porous matrix is a scaffolding of rutile-phase $TiO_2$ particles having platinum nanoclusters residing within the interstices between the $TiO_2$ particles. For other exemplary embodiments, the platinum nanoclusters are carried on the surface of the $TiO_2$ particles.

The porous matrix scaffolding is made by sintering a mass of metal oxide particles. In certain exemplary embodiments, the mass of metal oxide particles is a paste of metal oxide particles, which is thickly coated onto a substrate. The metal oxide particle paste is a mixture of appropriately sized metal oxide particles and a suitable medium, in a high enough concentration to give the mixture a paste-like viscosity. The medium used to make the paste is and it does not chemically react with the metal oxide particles or the substrate and it has a boiling point temperature that is less than the sintering temperature employed. A suitable medium includes, for example, but is not limited to, water, an alcohol, an organic solvent, or combinations thereof. A medium for certain exemplary embodiments is α-terpineol.

Since the metal oxide particle paste is coated onto a substrate, and since the substrate is heated to the sintering temperature along with the metal oxide particle paste, the substrate used should be thermally stable at the sintering temperature employed. In addition, as with the medium used to make the paste, the substrate should also be chemically inert. Suitable substrates include, but are not limited to, alumina, glass, silicon, quartz, and mixtures thereof. For certain exemplary embodiments, the substrate is alumina.

As the temperature is raised towards the sintering temperature, the medium evaporates away and a thick film of metal oxide particles is formed on the substrate. As the temperature is increased further, the individual metal oxide particles in the thick film come into contact and their surfaces become partially fused together. As a result, the thick film turns into a sintered mass that is held together at various locations throughout by particle-to-particle welds. This thick film/sintered mass eventually becomes, once sintering is complete, the porous matrix scaffolding. The metal oxide particles do not completely melt into a homogeneous, nonporous metal oxide layer. Rather, the temperature in sintering is kept low enough that the particles fuse together rather than melt. The sintered mass produced is porous and it retains most of the geometrical dimensionality and physical properties associated with the metal oxide particles.

Metal nanoclusters are then added into the porous matrix scaffolding (the sintered mass of metal oxide particles) and are intercalated into the interstices between the metal oxide particles. Metal nanoclusters can be added into the porous matrix scaffolding, for example, by impregnating the sintered mass of metal oxide particles with a dispersion of metal nanoclusters. Upon impregnation, the metal nanoclusters precipitate and deposit onto the surface of the metal oxide nanoparticles and are carried on the surface of the metal oxide particles. Since the dispersion may contain solvents or other organic compounds to help keep the nanoclusters dispersed, the impregnated sintered mass is subsequently cured to evaporate any volatile compounds introduced during impregnation and to pyrolyze any organic residues remaining. As a result, a porous matrix comprising a scaffolding of metal oxide particles and metal nanoclusters residing in the interstices between the metal oxide particles is produced. For certain exemplary embodiments of the composite, the porous matrix is made by sintering a mass of $TiO_2$ particles, impregnating this sintered mass with a dispersion of platinum nanoclusters, and then curing this impregnated mass to form the preferred Pt—$TiO_2$ porous matrix.

Metal nanoclusters dispersions can be made using known methods for producing metal colloids. For example, a method for producing platinum colloid employs a solution of dipotassium tetrachloroplatinate and combines this with a reducing agent to grown platinum nanoclusters in solution. This method is described in detail in L. D. Rampino, F. F. Nord, *Preparation of Palladium and Platinum Synthetic High-Polymer Catalysts and the Relationship between particle size and rate of hydrogenation*, J. Am. Chem. Soc. 63 (1941) 2745-2749, the entire disclosure which is herein incorporated by reference. Metal nanocluster dispersions, like the platinum colloid described, are used to impregnate a sintered mass of metal oxide particles. For example, a sintered mass of metal oxide particles can be impregnated by soaking it in a metal nanocluster dispersion or alternatively a metal nanocluster dispersion can be added dropwise onto the sintered mass in order to impregnate the sintered mass.

Optionally, a binder may be added to the metal nanocluster dispersion. The binder is a polymer or an oligomeric material added to the dispersion and it may assist the impregnation and composite formation in several respects. During preparation of a nanocluster dispersion, a binder may help to control the growth and size of the nanoclusters produced. At the pre-impregnation stage, a binder may help keep the metal nanoclusters dispersed and help prevent against nanocluster aggregation, agglomeration, or premature precipitation. During the impregnation stage, a binder may help to uniformly deposit the nanoclusters onto the metal oxide particle surface. Post-impregnation but before curing, the binder helps bond the metal nanoclusters to the metal oxide particles.

The binder is inert and does not chemically react with either the metal oxide particles or the metal nanoclusters. Also, it does not cause the metal nanoclusters to precipitate from the dispersion prematurely and it does not cause unacceptable agglomeration or aggregation of the metal nanoclusters either in the dispersion or on the surface of the metal oxide particles. A binder helps with obtaining a uniform distribution of metal nanoclusters bound to the metal oxide particle surfaces. Suitable binders include, but are not limited to, polyvinyl alcohol (PVA), polyvinyl pyrrolidone (PVP), and polyethyleneimine (PEI). For use in certain exemplary embodiments the binder is PVA.

The composite described above is used for making the detector and sensor devices provided herein. These devices comprise a pair of spaced electrodes and the previously described composite operatively connected to the pair of spaced electrodes. The electrodes can be in direct physical contact with the composite, or can be connected to the composite through EM communication between the electrodes and the composite. For example, EM communication includes, but is not limited to, electromagnetic induction, where the electrodes are coupled to the composite through a magnetic field, an electric field, or both.

The pair electrodes may also be interdigitated, which can be interdigited electrodes preprinted onto a support substrate. In an exemplary embodiment, a pair of electrodes is interdigitated electrodes preprinted onto a support substrate made from alumina. This same substrate is then used in the manner described above, and is the same substrate on which a paste of metal oxide particles is thickly coated and sintered to form a sintered mass of metal oxide particles. The sintered mass is now supported on the alumina substrate which has interdigitating electrodes residing on the substrate surface directly in contact with the sintered mass. The sintered mass is subsequently impregnated with metal nanocluster particles and cured to form a porous matrix of metal oxide-metal nanoclusters already operatively connected to a pair of spaced electrodes. In this fashion, device assembly is integrated directly into the procedure used to form the composite.

The electrodes are made of a conductive material which is inert and which does not chemically react with the metal oxide particles or the metal nanoclusters in the composite. Furthermore, when an interdigitating electrode pattern is pre-printed onto a substrate, the material used to print the electrodes is a material that is stable at the metal oxide particle sintering temperature. Suitable materials for the interdigitating electrodes include, for example, gold, palladium, platinum, and combinations thereof. For certain exemplary embodiments, the interdigitating electrodes are gold or platinum.

In order to function, the detector and sensor devices described herein utilize a property exhibited by the composite that when the composite is exposed to a gas mixture containing a reducing gas, for example, CO, the composite exhibits a change in electrical resistance proportional to the concentration of the reducing gas (i.e.; CO) present in the gas mixture. The resistance of the composite is measured for example by operatively connecting the device's electrodes to a voltmeter.

As such, whether a particular reducing gas is present in a surrounding gas mixture can be detected using the exemplary device arrangement described. For example, if the device is immersed in a gas mixture containing both $O_2$ and CO, the electrical resistance measured for the device will be lower than it would be if the gas mixture did not contain CO. As such, the device can be used to detect the presence of CO in a gas mixture. Furthermore, one of ordinary skill in the art will understand how to calibrate the device by systematically exposing the device to different gas mixtures that have concentrations of CO and $O_2$ that are previously known, and measuring the output of the device at the time of the different exposures to the different gas mixtures. Once calibrated, the device can then be used to measure the concentration of CO present in a test gas mixture, when the concentration of CO present in the test gas mixture is unknown.

The devices described herein exhibit the capability to detect and to measure the amount of CO present within an oxygen containing atmosphere. Furthermore, the devices derive this capability from the properties exhibited by the composite used to fabricate the devices. The composite exhibits an electrical resistance dependent upon the concentrations of gases present in the surrounding gas mixture. Consequently, it is believed that various embodiments of the composite herein described may likewise exhibit an electrical resistance dependent upon the concentrations of other types of reducing gases, gases similar to CO in terms of their ability to react with or be oxidized by oxygen ($O_2$), and/or other oxidizing reagents present in either a gas mixture or adsorbed onto the surface of the composition. Therefore, contemplated herein are detector and sensor devices that are capable of detecting and measuring reducing gases present in a gas mixture, the reducing gases are selected from the group consisting of $H_2$, hydrocarbons, CO, and combinations thereof. Both volatile aromatic and volatile aliphatic hydrocarbons are contemplated as reducing gases in this regard, including hydrocarbons selected from alkanes having the formula $C_2H_{2n+2}$, or alkenes having the formula $C_2H_{2n}$, wherein n=1-10.

In some embodiments, the detector and sensor devices described herein are capable of detecting CO present in a gas mixture. In other embodiments, the detector and sensor devices are capable of measuring the concentration of CO within a gas mixture containing $O_2$, when the CO is present in the gas mixture at concentrations of up to 10,000 ppm. According to some embodiments, the detector and sensor devices are capable of measuring the concentration of CO within a gas mixture containing $O_2$, when the CO is present in the gas mixture at concentrations of from 0 ppm to 10,000 ppm, and where the $O_2$ comprises from about 0.5% to about 21% of the gas mixture. The devices and sensors described herein are operable in temperatures ranging from about 450-700° C. According to some embodiments, the devices and sensors are operable in temperatures ranging from about 500-700° C. and have a recovery time of less than 1 minute.

Processes

Also provided herein is a process for detecting a reducing gas in a gas mixture. The process comprises operatively connecting a composite to a pair of spaced electrodes, exposing the composite to a gas mixture containing the reducing gas, and measuring the electrical resistance of the composite across the electrodes, while the composite is maintained at a temperature of at least 450° C. Any composite as described above is suitable for use with this process, including any of the exemplary embodiments herein mentioned.

Operatively connecting the composite to the pair of spaced electrodes puts the composite in electrical connection with the electrodes. For example, the electrodes may be physically attached to the composite directly, or the electrodes may be connected with the composite through establishing EM communication between the electrodes and the composite. This includes, but is not limited to, electromagnetic induction, wherein the electrodes are coupled to the composite through a magnetic field, an electric field, or both. In instances where a detector or sensor is fabricated from the composite, and device assembly is integrated directly into the procedure used to form the composite, the composite can be formed directly on a substrate already having interdigitating electrodes pre-printed onto the substrate surface making direct contact with the electrodes. The electrodes are therefore operatively connected to the composite as part of the composite formation process.

The process herein described is contemplated for detecting and measuring any of the reducing gases mentioned herein, including, reducing gases selected from the group consisting of $H_2$, hydrocarbons, CO, and mixtures thereof. The composite is exposed to the reducing gas when, as part of a device or a sensor, it is immersed into a gas mixture containing the reducing gas. The reducing gas may initially be present in the gas mixture when the composite is first exposed to the gas mixture or it may be introduced into the gas mixture at a later point, as for example, when the composite is located in an engine's exhaust system and the gas mixture is the exhaust gas from an engine, and the reducing gas is CO produced as combustion occurs within the engine. The process is suitable for use with gas mixtures having a broad temperature range from ambient temperature up to about 700° C. However, the gas mixture should contain oxygen.

The process herein described utilizes a composite having the property that, when exposed to a gas mixture containing a reducing gas, for example, CO, the composite exhibits a change in electrical resistance proportional to the concentration of the reducing gas (i.e.: CO) present. The resistance of the exposed composite is measured, for example, by operatively connecting a voltmeter to the pair of electrodes, which themselves are operatively connected to the composite, and observing the output of the voltmeter over time. A decrease in the resistance indicates the composite is detecting a reducing gas in the gas mixture. Whether a particular reducing gas is present or absent from the surrounding atmosphere can be detected using this exemplary device arrangement. Furthermore, one of ordinary skill in the art will understand how the device can be calibrated by exposure to different gas mixtures containing known concentrations of a reducing gas and measuring the electrical resistance output of the device over the course of the different exposures. Once the device is calibrated, the process described can be extended to measuring the concentration of a reducing gas present within a test gas mixture, when the concentration of reducing gas is unknown. Therefore, contemplated herein is a process for measuring the concentration of a reducing gas in a gas mixture. Specifically, contemplated is a process for measuring the concentration of a reducing gas in a gas mixture, wherein the reducing gas is selected from the group consisting of $H_2$, hydrocarbons, CO, and combinations thereof. The process is suitable for use with gas mixtures having a broad temperature range from ambient temperature up to about 700° C. However, the gas mixture should contain oxygen.

While the process is suitable for use in atmospheres over broad temperature ranges, from ambient to about 700° C., in order to be operable the composite itself must be at a temperature of at least 450° C., and must remain at this temperature during operation. The composite, as part of a detector or sensor for example, can be brought to this temperature by direct immersion in an environment of 450° C. or higher. This type of environment would be typical of the environments seen in the exhaust chamber of an engine for example. Alternatively, a separate heating unit could be directly attached to composite, as part of an extended device assembly, for example, and the composite could be heated to the operating temperature of at least 450° C.; independent of what the temperature is for the environment surrounding the device.

Provided herein is a process for detecting CO in a gas mixture. In some embodiments CO is measured within an oxygen-containing gas mixture, when the CO is present in the gas mixture at concentrations of from about 0-10,000 ppm. In some embodiments CO is measured within an oxygen-containing gas mixture at concentrations of from about 0-10,000 ppm, and where oxygen comprises from about 0.5% to about 21% of the gas mixture.

Methods

Also provided herein is a method for making a porous matrix comprising sintering a mass of metal oxide particles, impregnating the sintered mass with a dispersion of metal nanoclusters, and curing the impregnated sintered mass to form the porous matrix. The porous matrix comprises metal oxide particles and metal nanoclusters located within and/or residing in the interstices between the metal oxide particles. The porous matrix is an embodiment of the composite described herein. To make the porous matrix, a scaffolding of partially fused metal oxide particles is produced and this is then impregnated with the metal nanoclusters.

The porous matrix scaffolding is produced by sintering a mass of metal oxide particles. The mass is for example a paste of metal oxide particles made by dispersing appropriately size and shape metal oxide particles in a suitable medium in high enough concentration to provide a mixture having a paste-like viscosity. A substrate is thickly coated with the paste of metal oxide particles and heated. As the substrate and coating of paste is heated, sintering of the metal oxide particles occurs. As the temperature first increases, the medium evaporates and a thick film of metal oxide particles forms on the substrate. As the temperature increases further the individual metal oxide particles come into contact with each other and their surfaces partially fuse to one another, welding the thick film together at various locations throughout, and the structure eventually formed is the porous matrix scaffolding. Sintering continues until the particles are converted into the porous matrix scaffolding.

The metal oxide particles do not melt completely into a homogeneous, nonporous layer. Rather, the temperature is kept low enough that the particle surfaces only partially fuse together. The result is that the sintered mass produce is porous and it retains most of the geometrical dimensionality and physical properties associated with the metal oxide particles.

Metal nanoclusters are added to the porous matrix scaffolding (the sintered mass). The metal nanoclusters are intercalated into the interstices between the metal oxide particles. Metal nanoclusters can be added to the porous matrix scaffolding, for example, by impregnating the sintered mass with a dispersion of metal nanoclusters. Upon impregnation, the metal nanoclusters precipitate and deposit onto the metal oxide particles, being carried on the metal oxide particle surfaces. Subsequently, the impregnated mass is cured to evaporate any volatile compounds introduced during impregnation and to pyrolyze any organic residues remaining. In this manner a porous matrix comprising metal oxide particles and metal nanoclusters is produced.

Metal oxide particles suitable for use according to the method include, metal oxide particles selected from the group consisting of gallium oxide, tin oxide, titania, zinc oxide, indium oxide and combinations thereof. The metal oxide particles have a diameter of from about 0.1 μm to about 20 μm. In some embodiments, the metal oxide particles have a diameter of from about 0.5 μm to about 10 μm, in other embodiments a diameter of from about 1 μm to about 5 μm. Metal nanoclusters suitable for use according the method include, for example, but are not limited to, nanoclusters selected from Pt, Pd, Rh, Ru, Au, Ag, and Cu nanoclusters. Other suitable metal nanoclusters include and Ni—Au alloy, Cu—Au alloy, Co—Au alloy, and Ru—Sn alloy nanoclusters. Other suitable metal nanoclusters can be made from copper oxide and copper-cerium oxides, copper-manganese oxides, and catalysts such as ruthenium oxide, $CuMn_2O_4$ (hopcalite), and $CuCoAgMnO_x$ mixed oxides. The metal nanoclusters have a diameter of from about of from about 1 nm to about 500 nm. In some embodiments, the metal nanoclusters have a diameter of from about 10 nm to about 100 nm.

One method for making a porous matrix comprises sintering a mass of $TiO_2$ particles, impregnating the sintered mass with a dispersion of platinum nanoclusters, and curing the impregnated sintered mass to form the porous matrix. According to some methods, the $TiO_2$ particles have a diameter of from about 1 μm to about 5 μm. According to other methods, the $TiO_2$ particles have a diameter of from about 1 μm to about 5 μm and the platinum nanoclusters have a diameter of from about 10 nm to about 100 nm.

Since for certain embodiments the porous matrix is the composite described herein, the method for making a porous matrix is also a method for making a composite. In this respect, also contemplated is a method for making a composite comprising applying a paste of metal oxide particles onto a substrate, sintering the paste to form a porous film of metal oxide on the substrate; impregnating the porous film with a dispersion comprising metal nanoclusters and curing the impregnated porous film to form the composite. Optionally, the dispersion used to impregnate the porous film also comprises a binder. A suitable binder has been described earlier and include any binder herein mentioned.

One method for making a composite comprises applying a paste of $TiO_2$ particles onto a substrate, sintering the paste to form a porous film of rutile-phase $TiO_2$ on the substrate, impregnating the porous film of rutile-phase $TiO_2$ with a dispersion comprising platinum nanoclusters; and curing the impregnated porous film of rutile-phase $TiO_2$ to form the composite. Optionally, the dispersion used to impregnate the porous film of rutile-phase $TiO_2$ also comprises a binder. In some embodiments, the binder is polyvinyl alcohol.

Devices

Since for certain embodiments the porous matrix is the composite described herein, it is also a component of various embodiments of detector and sensor devices described herein. Therefore, methods for making a detector or sensor device can include the method for making a porous matrix.

In this respect, also herein contemplated is a method for making a device for detecting a reducing gas in a gas mixture or for measuring the amount of a reducing gas in a gas mixture, the method comprising sintering a mass of metal oxide particles, impregnating the sintered mass with a dispersion of metal nanoclusters, curing the impregnated sintered mass to form a porous matrix, and operatively connecting a pair of spaced electrodes to the porous matrix. Alternatively, the method for making a device for detecting a reducing gas in a gas mixture or measuring the amount of a reducing gas in a gas mixture comprises: applying a paste of metal oxide particles onto a substrate, wherein a set of interdigitated electrodes are present on the surface of the substrate physically contacting the paste, sintering the paste to form on the substrate a porous film of metal oxide that is operatively connected to the set of interdigitated electrodes; impregnating the porous film with a dispersion comprising metal-based nanoclusters and a binder; and curing the impregnated porous film to form the device.

One method for making a CO sensor comprises sintering a mass of $TiO_2$ particles, impregnating the sintered mass with a dispersion of platinum nanoclusters, curing the impregnated sintered mass to form a porous matrix, and operatively connecting a pair of spaced electrodes to the porous matrix. In another embodiment, the method for making a CO sensor comprises: applying a paste of $TiO_2$ particles onto a substrate, wherein a set of interdigitated electrodes are present on the surface of the substrate physically contacting the paste; sintering the paste to form on the substrate a porous film of rutile-phase $TiO_2$ which is operatively connected to the set of interdigitated electrodes; impregnating the porous film of rutile-phase $TiO_2$ with a dispersion comprising platinum nanoclusters and polyvinyl alcohol; and curing the impregnated porous film of rutile-phase $TiO_2$ to form the CO sensor.

Examples

Materials

Rutile $TiO_2$ particles: Anatase $TiO_2$ powder (99.9% Aldrich) was used as the raw material used to fabricate the examples. The as received anatase $TiO_2$ powder was dispersed in isopropanol and ultrasonicated for about 30 min to de-agglomerate the particles. The slurry was dried in a rotovap and cured at 800° C. for 6 hours. The collected powder was annealed again at 1000° C. for 24 hours at a heating and cooling rate of 5° C./min, and a powder of $TiO_2$ particles was obtained in the rutile phase. XRD analysis confirms the anatase and rutile phases before and after the annealing treatment.

Platinum colloid-PVA dispersion: Colloidal platinum stabilized with PVA was prepared by using a technique first described by Rampino and Nord [0035] with slight modifications. Twenty-three mg of dipotassium tetrachloroplatinate was added to 2 ml of deionized water. A separate 2% polyvinyl alcohol (PVA) solution was made by adding 500 mg of PVA in small amounts to 25 ml of stirred deionized water kept at 80° C. Stirring and heating was maintained for 2 to 3 hours until the solution was clear. Once the solution was cooled, it was filtered through glass wool. 12.5 ml of the 2% PVA solution was placed in a flask, stirred, and 11 ml of water added to it. To this new solution, 1 ml of the aqueous 0.5% Pt solution was added slowly in a dropwise manner under fast stirring. 0.4 ml of a 4% NaOH solution was added in a dropwise manner, and the solution heated to boiling for 5 minutes then cooled to room temperature. To this dark solution, 4 mg of sodium borohydride was added to reduce the dissolved platinum species to colloidal platinum and stirred overnight. A sample of titania with colloidal platinum was made by taking 0.8 g of titania and combining it with 4.2 ml of the PVA-Pt solution (resulting in 0.1 wt % overall Pt). This suspension was then sonicated for an hour with periodic shaking in order to combine the layers thoroughly. The suspension was transferred to a flask, stirred, and heated briefly. Portions of this suspension were then added dropwise to the rutile on the alumina substrate.

Preparation

The various sensor components and a schematic for the sensor preparation is shown in FIG. 1. Briefly, the example CO sensors were prepared as follows. The powder of rutile $TiO_2$ particles was mixed with alpha-terpeneol to make a paste. A thick coating of paste was painted onto two separate alumina substrates that have gold or platinum interdigitated electrodes printed on the surface, one substrate was used for the working example (the Pt—$TiO_2$ sensor) and one substrate was used for the comparative example (the control sensor). The painted thick film on the comparative example substrate was sintered at 800° C. for two hours to form the control sensor. The painted thick film on the working example substrate was also sintered at 800° C. for two hours. Then the platinum colloid-PVA dispersion (described above) was added drop-wise onto the sintered working example substrate using a syringe. This was followed by a curing treatment at 650° C. for 2 hours to form the Pt—$TiO_2$ sensor.

Characterization

General

Surface morphology of films made from the rutile-phase $TiO_2$ particles before and after platinum nanocluster addition was examined by using SEM (Phillips XL 30 ESEM FEG). The surface chemical states of the elements were identified by using XPS spectrometer (Kratos). Dynamic changes in the electrical resistance of rutile-phase $TiO_2$ particle films with and without platinum nanoclusters dispersed on the $TiO_2$ particle surface were studied by gas sensing experiments at 600° C. Air and nitrogen gas cylinders were used to provide gaseous environments with different concentrations of $O_2$ (via. 21, 10, 5, 3 and 2%) in the flowing gas. With a fixed oxygen level in the gas flow, say 10%, CO gas was admitted in different concentrations via. 10, 50, 100, 250 and 500 ppm along with the carrier gas $O_2/N_2$. The rutile-phase $TiO_2$ particle films were physically connected to two electrode wires and these devices were placed in a quartz tube reactor of 4 cm diameter and 40 cm long kept at high temperature. The net gas flow was set at 100 cc/min for all experiments. The data acquisition was performed by using HP multimeter and BenchLink software.

Morphology

Figure 2:
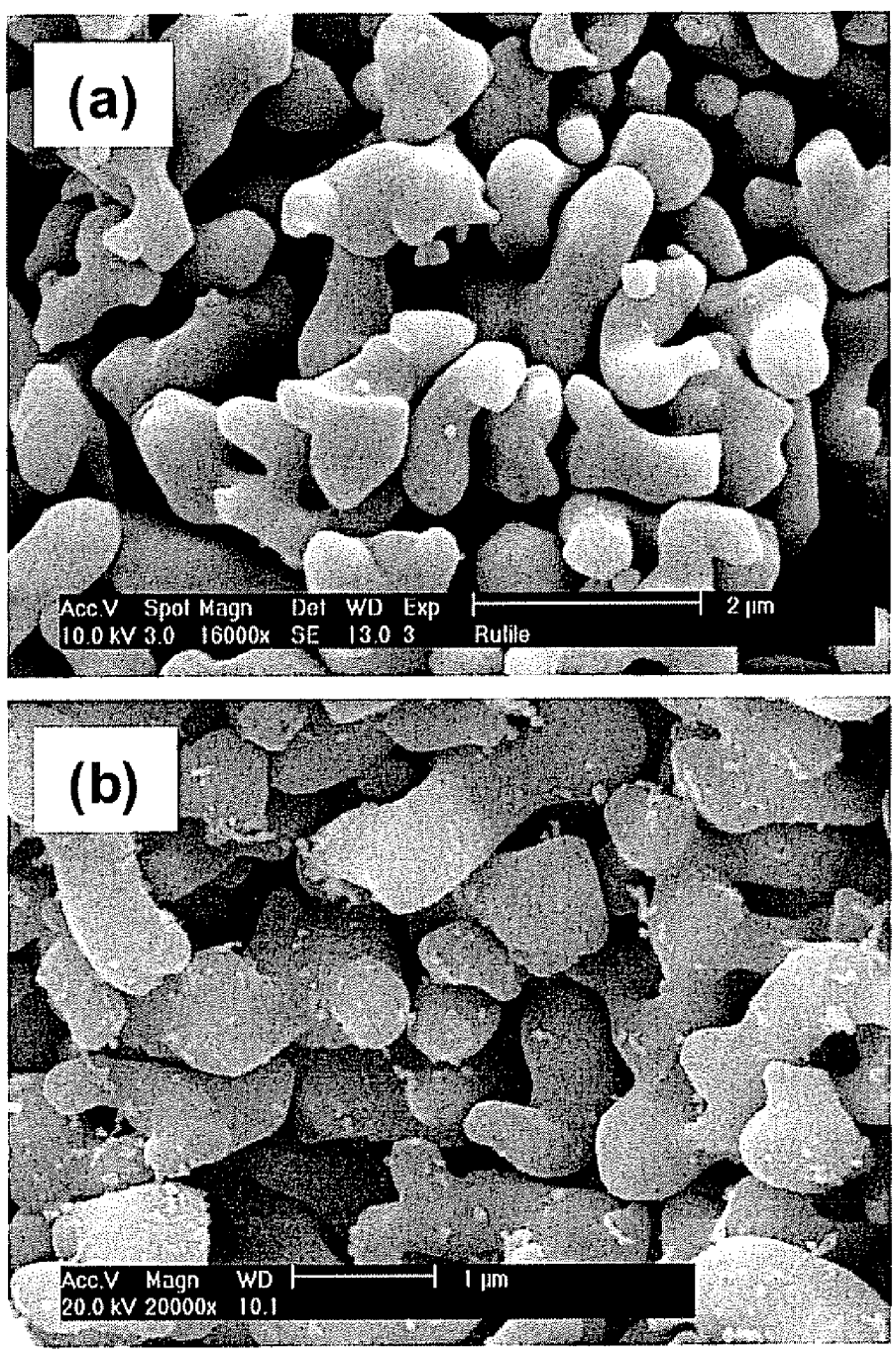
FIG. 2 shows SEM micrographs for (a) a rutile-phase $TiO_2$ film and (b) a Pt—$TiO_2$ composite film.
Figure 3:
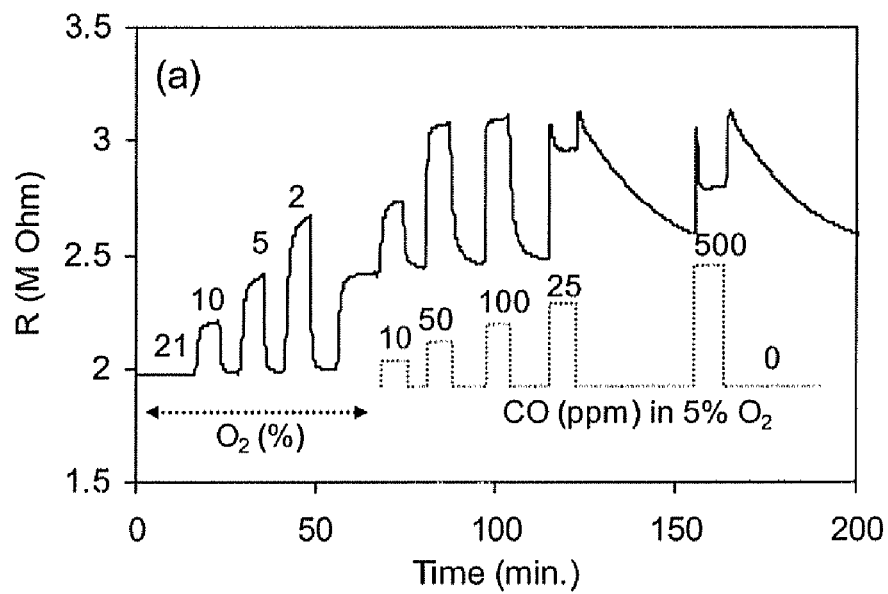
FIG. 3 shows dynamic electrical resistance response plots for (a) a rutile-phase $TiO_2$ film and (b) a Pt—$TiO_2$ composite film upon exposure to varying CO and $O_2$ concentrations.
Figure 3:
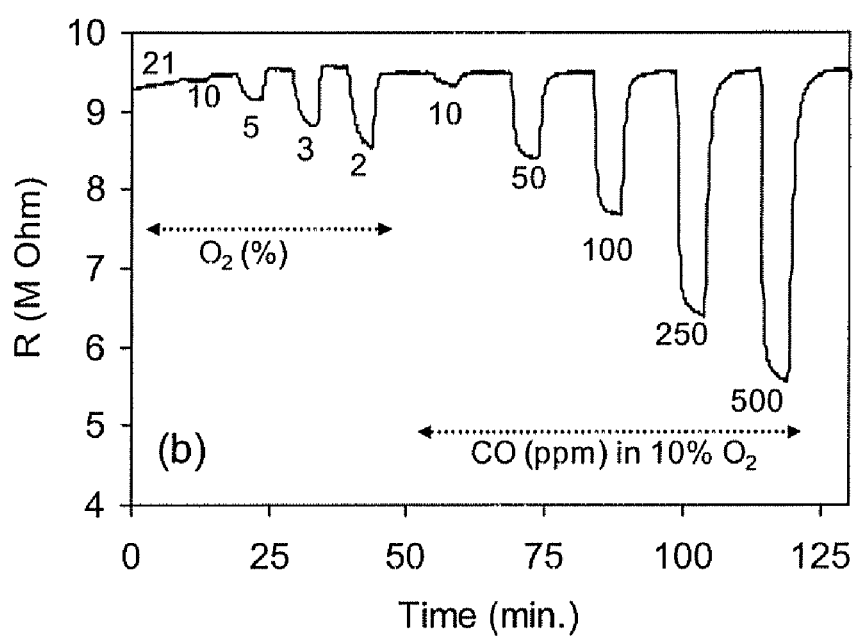

Sample films made from the rutile-phase $TiO_2$ particles prepared in the manner described above were subjected for microstructural observations by using SEM. Shown in FIG. 2 are the SEM micrographs of rutile-phase $TiO_2$ particle films used in fabricating the control sensor (FIG. 2a) and the platinum nanocluster impregnated rutile-phase $TiO_2$ particle film used in fabricating Pt—$TiO_2$ sensor (FIG. 2b). The SEM micrograph FIG. 2a shows uncoated rutile $TiO_2$ particles of irregular shape and that are on the order of a few microns in size. The SEM micrograph FIG. 2b shows platinum colloidal particles of about 20 nm in size distributed all over the rutile-phase $TiO_2$ particles in the sample. Attempts to quantify the amount of platinum dispersion on the titania matrix approximated that platinum nanoclusters covered about 5-10% the rutile-phase $TiO_2$ particle surface Properties FIG. 3 shows the dynamic gas-sensing response transients to $O_2$ and CO at 600° C. for the control sensor (FIG. 3a) and the Pt—$TiO_2$ sensor (FIG. 3b).

FIG. 3a shows, as the $O_2$ is decreased from 21% to 2%, the electrical resistance for the control sensor increases. The control sensor also initially responds with a resistance increase with increasing CO gas. However, at higher concentrations of CO, ca.>250 ppm, the response changes. Specifically, when CO is present in concentrations of above 250 ppm CO the steady state resistance decreases indicating that the electronic properties of the rutile-phase $TiO_2$ particle film are altered when exposed to CO concentrations above 250 ppm. The increasing resistance with decreasing oxygen levels from 21% through 2%, and the different responses of the material to CO concentrations from 10 ppm to 250 ppm, as compared with CO levels above 250 ppm indicate there are several threshold concentrations where the electrical resistance of undoped rutile-phase $TiO_2$ film changes upon exposure to different gases. This makes undoped rutile-phase $TiO_2$ unreliable and therefore unsuitable for use as a sensor material since any sensor made from this material would likely behave unreliably. FIG. 3a also shows that undoped rutile-phase $TiO_2$ exhibits other anomalies which also make it an unsuitable sensor material. At CO concentrations of 500 ppm and above, erratic spikes of resistance are seen as CO is introduced and removed from the gas mixture. Also, the material exhibits very slow recovery time once CO is removed from the gas mixture (on the order of 20-30 minutes).

FIG. 3b shows that upon doping with platinum nanoclusters, the electrical response and the sensitivity of the Pt—$TiO_2$ sensor (the Pt doped $TiO_2$ film) is completely different with respect to the presence of both oxygen and CO as compared to the control sensor (the undoped rutile-phase $TiO_2$ film). The presence of platinum nanoclusters deposited on the surface of the $TiO_2$ particles leads to two significant changes in the electrical properties and gas sensitivity for the Pt doped $TiO_2$ film compared with the undoped rutile-phase $TiO_2$ film. Under similar conditions of temperature and alterations in gas concentration the Pt doped $TiO_2$ film exhibits (1) reduced oxygen sensitivity and (2) improved recovery characteristics. FIG. 3b shows that there is a drastic decrease in recovery time upon removal of CO from the gas stream. The recovery time for the Pt—$TiO_2$ sensor made from the Pt doped $TiO_2$ film is less than 1 minute compared to the more than 20 minutes for the control sensor made from the undoped $TiO_2$ film. This comparison indicates that dispersing platinum monclusters of size range 10-100 nm onto rutile-phase $TiO_2$ particles produces a composite, which is useful for forming a CO sensor that behaves reliably over a broad range of CO concentrations.

Figure 4:
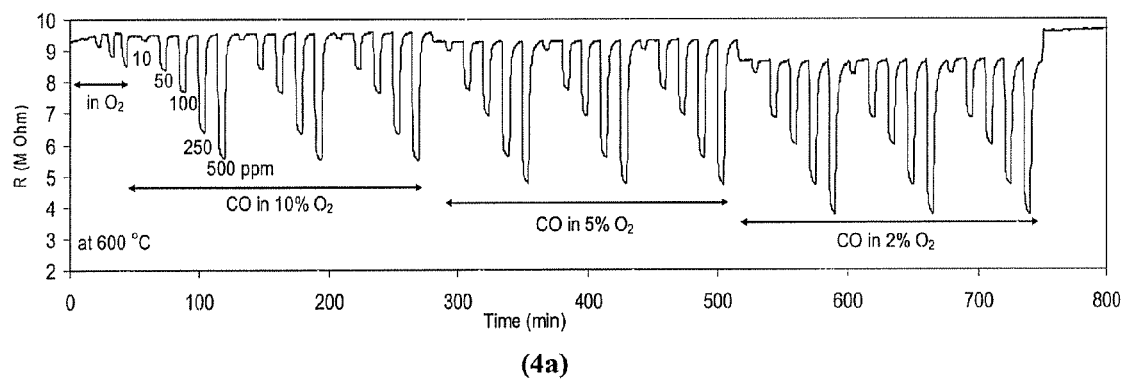
FIG. 4 shows a dynamic electrical resistance response plot for a Pt—$TiO_2$ composite film upon exposure to various levels of $O_2$ and CO at (a) 10-500 ppm (b) 1-10 ppm.
Figure 4:
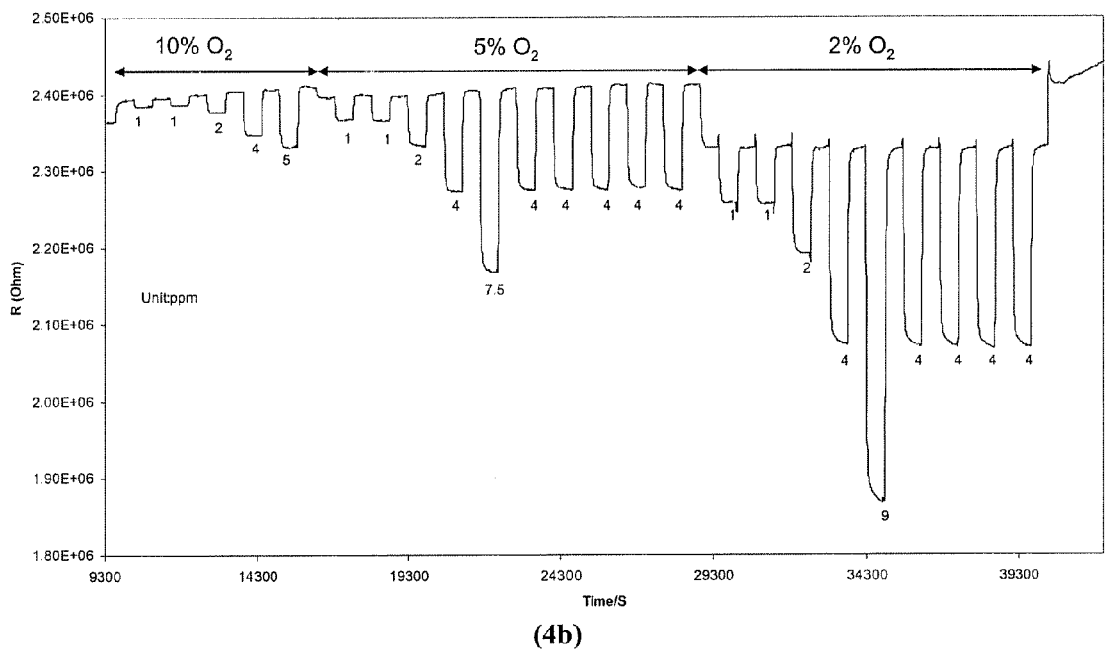

The Pt—$TiO_2$ sensor has sensing capability for the range of CO levels from 0-10,000 ppm, and is stable, reproducible, and fast compared to other sensors based on $TiO_2$. The sensor operates in the temperature range from 450° C. to 700° C. in gas mixtures containing oxygen and CO. CO levels of 1, 2, 4, 5, 7.5, 9, 10, 50, 100, 250 and 500 ppm can be detected in different oxygen background levels of 10, 5, and 2% in nitrogen. FIGS. 4a-b shows the dynamic response of the Pt—$TiO_2$ sensor at 600° C. in the range from 1-500 ppm CO.

Device sensitivity is determined by examining the gas dependent response of the electrical resistance. The manifestation of the resistance with the change of oxygen partial pressure $pO_2$ and with change of CO concentration [CO] is represented by:

$$R\alpha(pO_2)^{1/m} \quad (1)$$

and $$R/R_0\alpha[CO]^{1/\beta} \quad (2)$$

where R and $R_0$ are the resistance values in presence and absence (only with reference gas) of the test gas, m and $\beta$ are the exponents called sensitivity parameters for $O_2$ and CO respectively. For CO sensing, the sensitivity can be represented in the same way as for oxygen by the slope $(1/\beta)$ of log $R/R_0$ vs. log [CO] plot, where R and $R_0$ are the resistance values of the sensor in the presence and the absence of the test gas respectively. The lower the value of $|\beta|$, higher is the sensitivity to CO.

Figure 5:
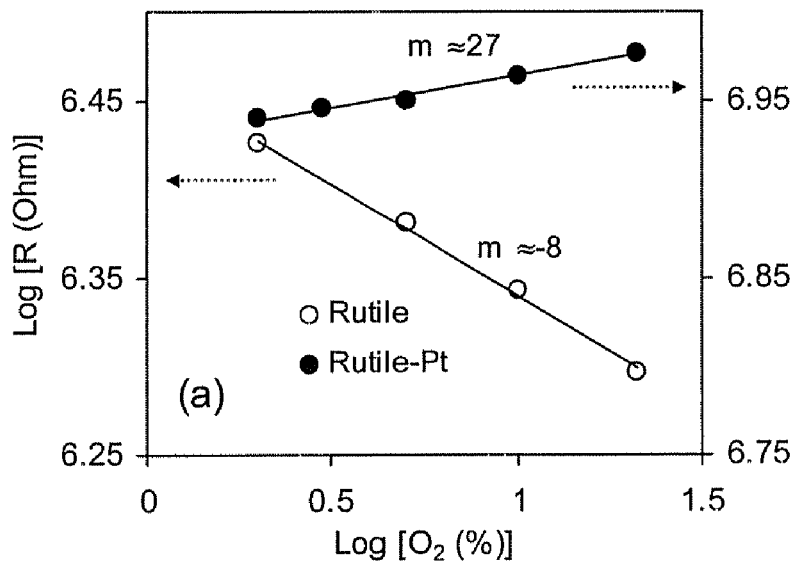
FIG. 5 shows plots comparing the sensitivity of a rutile-phase $TiO_2$ film with a Pt—$TiO_2$ composite film to (a) various levels of $O_2$ and (b) various levels of CO.
Figure 5:
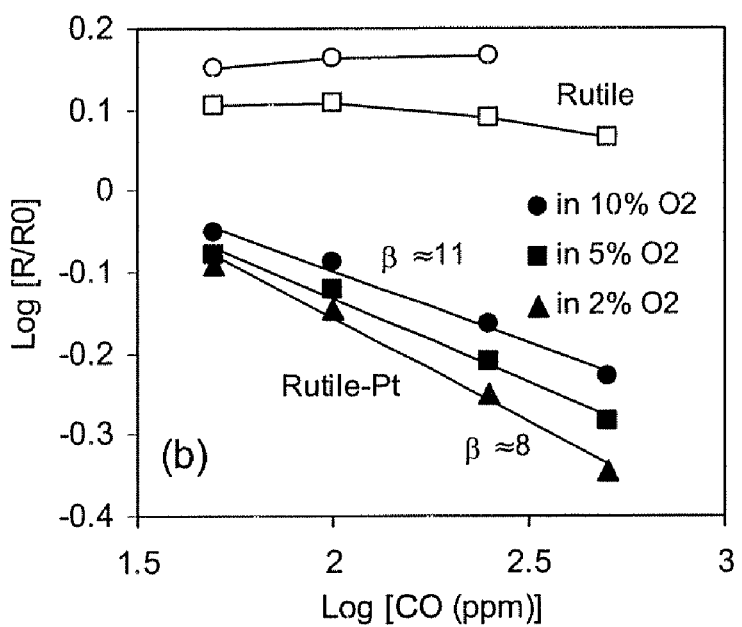

FIGS. 5a and 5b compares the sensitivity of the control sensor (Rutile) with that of the Pt—$TiO_2$ sensor (Rutile-Pt). FIG. 5a plots the sensitivity response of the resistance changes with different oxygen concentrations at 600° C. for the control sensor (Rutile) and Pt—$TiO_2$ sensor (Rutile-Pt). FIG. 5b plots the sensitivity response of the resistance changes with different oxygen and CO concentrations at 600° C. for the control sensor (Rutile) and Pt—$TiO_2$ sensor (Rutile-Pt). As can be seen in FIG. 5a, the oxygen sensitivity parameter m takes values of −8 for the control sensor (Rutile) and 27 for the Pt—$TiO_2$ sensor (Rutile-Pt). This means that the oxygen sensitivity for the Pt—$TiO_2$ sensor is reduced (1/27) compared with the control sensor (1/8). On the other hand, FIG. 5b shows that the CO sensitivity of the Pt—$TiO_2$ sensor is much larger, in the range of 1/11-1/8, compared with the control sensor.

Typical titania-based devices exhibit two common problems associated with detecting and sensing of CO (1) slow recovery times and (2) significant interference from $O_2$. The example sensor described herein overcomes these two problems exhibiting an improved response time, an improved recovery time, and a reduced sensitivity to $O_2$ as compared with other titania-based sensors, like the control sensor herein described. A unique composite comprising rutile-phase $TiO_2$ particles and platinum colloids or nanoclusters deposited on the surface of the $TiO_2$ particles provides for fabrication of a CO sensor that exhibits stable and reproducible behavior.

The examples described herein are for illustration only and are not meant to limit the scope of the invention as defined in the claims.

Exemplary Embodiments

Exemplary embodiments of the invention include, but are not limited to:

1. A composite comprising rutile-phase $TiO_2$ particles and platinum nanoclusters wherein the composite, when exposed to a gas mixture containing carbon monoxide, exhibits an electrical resistance which is proportional to the concentration of carbon monoxide present in the gas mixture.
2. A composite according to embodiment 1, wherein the composite is made from a porous matrix comprising rutile-phase $TiO_2$ particles and platinum nanoclusters residing within the interstices between the $TiO_2$ particles.
3. A composite according to any one embodiment of the preceding embodiments, wherein the platinum nanoclusters are carried on the surface of the $TiO_2$ particles.
4. A composite according to any one embodiment of the preceding embodiments, wherein the $TiO_2$ particles have a diameter of from about 1 μm to about 5 μm.
5. A composite according to any one embodiment of the preceding embodiments, wherein the platinum nanoclusters have a diameter of from about 10 nm to about 100 nm.
6. A composite according to any one embodiment of the preceding embodiments, wherein the porous matrix is made by sintering a mass of $TiO_2$ particles, impregnating the sintered mass with a dispersion of platinum nanoclusters, and curing the impregnated sintered mass to form the porous matrix.
7. A composite according to any one embodiment of the preceding embodiments, wherein the mass is a paste of the $TiO_2$ particles.
8. A composite comprising metal oxide particles and metal nanoclusters wherein the composite, when exposed to a gas mixture containing a reducing gas, exhibits an electrical resistance which is proportional to the concentration of the reducing gas present in the gas mixture.
9. A composite according to embodiment 8, wherein the composite is made from a porous matrix comprising metal oxide particles and metal nanoclusters residing within the interstices between the metal oxide particles.
10. A composite according to any one embodiment of embodiment 8 through the immediately preceding embodiment, wherein the metal nanoclusters are carried on the surface of the metal oxide particles.
11. A composite according to any one embodiment of embodiment 8 through the immediately preceding embodiment, wherein the metal oxide particles have a diameter of from about 1 tin to about 5 μm.
12. A composite according to any one embodiment of embodiment 8 through the immediately preceding embodiment, wherein the metal nanoclusters have a diameter of from about 10 nm to about 100 nm.
13. A composite according to any one embodiment of embodiment 8 through the immediately preceding embodiment, wherein the porous matrix is made by sintering a mass of metal oxide particles, impregnating the sintered mass with a dispersion of metal-containing nanoclusters, and curing the impregnated sintered mass to form the porous matrix.
14. A composite according to embodiment 13, wherein the mass is a paste of the metal oxide particles.
15. A composite according to any one embodiment of embodiment 8 through the immediately preceding embodiment, wherein the metal oxide is selected from the group consisting of gallium oxide, tin oxide, titanium dioxide, zinc oxide, and mixtures thereof.

16. A composite according to any one embodiment of embodiment 8 through the immediately preceding embodiment, wherein the metal nanoclusters are selected from the group consisting of Pt, Pd, Rh, Ru, Au, Ag, and Cu and mixtures thereof.

17. A composite according to any one embodiment of embodiment 8 through the immediately preceding embodiment, wherein the metal nanoclusters are metal-alloy nanoclusters selected from the group consisting of Ni—Au alloy, Cu—Au alloy, Co—Au alloy, and Ru—Sn alloy and mixtures thereof.

18. A composite according to any one embodiment of embodiment 8 through the immediately preceding embodiment, wherein the metal nanoclusters are metal nanoclusters containing copper oxide, copper-cerium oxide, copper-manganese oxide, and mixtures thereof.

19. A composite according to any one embodiment of embodiment 8 through the immediately preceding embodiment, wherein the nanoclusters are metal oxide nanocluster catalysts selected from ruthenium oxide, $CuMn_2O_4$ (hopcalite), $CuCoAgMnO_x$, and mixtures thereof.

20. A composite according to any one embodiment of embodiment 8 through the immediately preceding embodiment, wherein the reducing gas is selected from the group consisting of $H_2$, hydrocarbon gas, CO, and mixtures thereof.

21. A composite according to embodiment 20, wherein the hydrocarbon gas is an aromatic hydrocarbon.

22. A composite according to embodiment 20, wherein the hydrocarbon gas is selected from alkanes having the formula $C_2H_{2+2}$, or alkenes having the formula $C_2H_{2n}$, and wherein n=1-10.

23. A device comprising a pair of spaced electrodes and a composite according to any one embodiment of the preceding embodiments operatively connected to the pair of spaced electrodes.

24. A device according to any one embodiment of the preceding embodiments, wherein the composite is in physical contact with the pair of spaced electrodes.

25. A device according to any one embodiment of the preceding embodiments, wherein the pair of spaced electrodes is interdigitated and supported on a substrate.

26. A device according to any one embodiment of the preceding embodiments, wherein the substrate is selected from the group consisting of alumina, glass, silicon, quartz, and mixtures thereof.

27. A detector device comprising the device of any one embodiment 23 through the immediately preceding embodiment.

28. A sensor device comprising the device of any one embodiment 23 through the immediately preceding embodiment.

29. A device according to any one embodiment of embodiment 23 through the immediately preceding embodiment operatively connected to a voltmeter.

30. A detector device according to any one embodiment of embodiment 23 through the immediately preceding embodiment, capable of selectively detecting carbon monoxide in a gas mixture.

31. A sensor device according to any one embodiment of embodiment 23 through the immediately preceding embodiment, capable of measuring the concentration of carbon monoxide within a gas mixture when the carbon monoxide is within the gas mixture at concentrations of up to 10,000 ppm.

32. A hydrogen detector device according to any one embodiment of embodiment 23 through the immediately preceding embodiment, capable of selectively detecting hydrogen in a gas mixture.

33. A hydrocarbon detector device according to any one embodiment of embodiment 23 through the immediately preceding embodiment, having a capability to selectively detect hydrocarbon gas in a gas mixture.

34. A device according to any one embodiment of embodiment 23 through the immediately preceding embodiment, having operability in a temperature range of from about 450-700° C.

35. A device according to any one embodiment of embodiment 23 through the immediately preceding embodiment, having a recovery time of less than 1 minute.

36. A process for selectively detecting carbon monoxide in a gas mixture comprising:
   a. operatively connecting a composite to a pair of spaced electrodes, wherein the composite is a composite according to any one embodiment of embodiment 1 through embodiment 19;
   b. exposing the composite to a gas mixture containing carbon monoxide; and
   c. measuring the electrical resistance of the composite across the electrodes, while the composite is maintained at a temperature of at least 450° C.

37. A process for measuring carbon monoxide in a gas mixture at concentrations of from about 0-10,000 ppm, comprising:
   a. operatively connecting a composite to a pair of spaced electrodes, wherein the composite is a composite according to any one embodiment of embodiment 1 through embodiment 19;
   b. exposing the composite to a gas mixture containing carbon monoxide; and
   c. measuring the electrical resistance of the composite across the electrodes, while the composite is maintained at a temperature of at least 450° C.

38. A process for selectively detecting a reducing gas in an atmosphere comprising:
   a. operatively connecting a composite to a pair of spaced electrodes, wherein the composite is a composite according to any one embodiment of embodiment 1 through embodiment 19;
   b. exposing the composite to a gas mixture containing the reducing gas; and
   c. measuring the resistance of the composite across the electrodes, while the composite is maintained at a temperature of at least 450° C.

39. A process according to any one embodiment of embodiment 36 through the immediately preceding embodiment, wherein the gas mixture contains oxygen in concentrations of from about 0.5% to about 21%.

40. A process according to any one embodiment of embodiment 36 through the immediately preceding embodiment, wherein the reducing gas is selected from the group consisting of $H_2$, hydrocarbons, CO, and mixtures thereof.

41. A method for making a porous matrix comprising sintering a mass of $TiO_2$ particles, impregnating the sintered mass with a dispersion of platinum nanoclusters, and curing the impregnated sintered mass to form the porous matrix.

42. A method for making a porous matrix comprising sintering a mass of metal oxide particles, impregnating the sintered mass with a dispersion of metal nanoclusters, and curing the impregnated sintered mass to form the porous matrix.

43. A method for making a device for selectively detecting and measuring carbon monoxide comprising sintering a mass of TiO$_2$ particles, impregnating the sintered mass with a dispersion of platinum nanoclusters, curing the impregnated sintered mass to form a porous matrix, and operatively connecting a pair of spaced electrodes to the porous matrix.

44. A method for making a detector device for selectively detecting and measuring a reducing gas comprising sintering a mass of metal oxide particles, impregnating the sintered mass with a dispersion of metal nanoclusters, curing the impregnated sintered mass to form a porous matrix, and operatively connecting a pair of spaced electrodes to the porous matrix.

45. A method for making a composite comprising:
    a. applying a paste of TiO$_2$ particles onto a substrate;
    b. sintering the paste to form a porous film of rutile-phase TiO$_2$ on the substrate;
    c. impregnating the porous film with a dispersion comprising:
        i. platinum nanoclusters, and
        ii. a binder; and
    d. curing the impregnated porous film to form the composite.

46. A method for making a composite comprising:
    a. applying a paste of metal oxide particles onto a substrate;
    b. sintering the paste to form a porous film of metal oxide on the substrate;
    c. impregnating the porous film with a dispersion comprising:
        i. metal-based nanoclusters, and
        ii. a binder; and
    d. curing the impregnated porous film to form the composite.

47. A method according to any one embodiment of embodiment 45 through the immediately preceding embodiment, wherein a set of interdigitated electrodes reside on the surface of the substrate physically contacting the paste.

48. A method for making a device for selectively detecting and measuring carbon monoxide comprising:
    a. applying a paste of TiO$_2$ particles onto a substrate having a set of interdigitated electrodes printed on the surface of the substrate which is in physical contact with the paste;
    b. sintering the paste to form a porous film of rutile-phase TiO$_2$ on the substrate and operatively connected to the set of interdigitated electrodes
    c. impregnating the porous film with a dispersion comprising:
        i. platinum nanoclusters, and
        ii. a binder; and
    d. curing the impregnated film to form the device.

49. A method for making a device for selectively detecting and measuring a reducing gas comprising:
    a. applying a paste of metal oxide particles onto a substrate having a set of interdigitated electrodes printed oil the surface of the substrate which is in physical contact with the paste;
    b. sintering the paste to form a porous film of metal oxide on the substrate and operatively connected to the set of interdigitated electrodes;
    c. impregnating the porous film with a dispersion comprising:
        i. metal-based nanoclusters, and
        ii. a binder; and
    d. curing the impregnated porous film to form the device.

50. A method according to any one embodiment of embodiment 41 through the immediately preceding embodiment, wherein the metal oxide is selected from the group consisting of gallium oxide, tin oxide, TiO$_2$, zinc oxide, and mixtures thereof.

51. A method according to any one embodiment of embodiment 41 through the immediately preceding embodiment, wherein the TiO$_2$ particles have a diameter of from about 1 μm to about 5 μm.

52. A method according to any one embodiment of embodiment 41 through the immediately preceding embodiment, wherein the metal oxide particles have a diameter of from about 1 μm to about 5 μm.

53. A method according to any one embodiment of embodiment 41 through the immediately preceding embodiment, wherein the metal nanoclusters are selected from the group consisting of Pt, Pd, Rh, Ru, Au, Ag, and Cu and mixtures thereof.

54. A method according to any one embodiment of embodiment 41 through the immediately preceding embodiment, wherein the metal nanoclusters are metal-alloy nanoclusters selected from the group consisting of Ni—Au alloy, Cu—Au alloy, Co—Au alloy, and Ru—Sn alloy and mixtures thereof 55. A method according to any one embodiment of embodiment 41 through the immediately preceding embodiment, wherein the metal nanoclusters are metal nanoclusters containing copper oxide, copper-cerium oxide, copper-manganese oxide, and mixtures thereof.

56. A method according to any one embodiment of embodiment 41 through the immediately preceding embodiment, wherein the metal nanoclusters are metal nanocluster catalysts selected from ruthenium oxide, CuMn$_2$O$_4$ (hopcalite), CuCoAgMnO$_x$, and mixtures thereof.

57. A method according to any one embodiment of embodiment 41 through the immediately preceding embodiment, wherein the platinum nanoclusters have a diameter of from about 10 nm to about 100 nm.

58. A method according to any one embodiment of embodiment 41 through the immediately preceding embodiment, wherein the metal oxide nanoclusters have a diameter of from about 10 nm to about 100 nm.

59. A method according to any one embodiment of embodiment 45 through the immediately preceding embodiment, wherein the binder is a polymer selected from polyvinyl alcohol, polyvinyl pyrrolidone, and polyethyleneimine.

The invention claimed is:

1. A composite comprising metal oxide particles and metal nanoclusters, wherein the composite when exposed to a gas mixture containing a reducing gas exhibits an electrical resistance which is proportional to the concentration of the reducing gas present in the gas mixture, wherein the metal oxide particles are rutile-phase TiO$_2$ particles and the metal nanoclusters are platinum nanoclusters, and wherein the composite when exposed to a gas mixture containing carbon monoxide exhibits an electrical resistance which is proportional to the concentration of carbon monoxide present in the gas mixture.

2. The composite of claim 1, wherein the composite is made from a porous matrix comprising a scaffolding of rutile-phase TiO$_2$ particles and platinum nanoclusters located within the interstices between the TiO$_2$ particles.

3. The composite of claim 2, wherein the TiO$_2$ particles have a diameter of from about 1 μm to about 5 μm.

4. The composite of claim 3, wherein the platinum nanoclusters are carried on the surface of the TiO$_2$ particles.

5. The composite of claim 4, wherein the platinum nanoclusters have a diameter of from about 10 nm to about 100 nm.

6. The composite of claim 2, wherein the porous matrix is made by sintering a mass of $TiO_2$ particles, impregnating the sintered mass with a dispersion of platinum nanoclusters, and curing the impregnated sintered mass to form the porous matrix.

7. The composite of claim 6 operatively connected to a pair of spaced electrodes.

8. The composite of claim 7, wherein the pair of spaced electrodes is interdigitated and supported on a substrate.

9. The composite of claim 8, wherein the substrate is selected from the group consisting of alumina, glass, silicon, quartz, and mixtures thereof.

10. A detector device comprising the composite of claim 9, capable of selectively detecting carbon monoxide in a gas mixture.

11. A sensor device comprising the composite of claim 9, capable of measuring carbon monoxide in a gas mixture.

12. The sensor device of claim 11, capable of measuring carbon monoxide in a gas mixture when carbon monoxide is present in the gas mixture at concentrations of up to 10,000 ppm.

13. The device of claim 12, operable in a temperature range of from about 450-700° C.

14. The device of claim 13 having a recovery time of less than 1 minute.

15. A process for measuring carbon monoxide in a gas mixture comprising:
   a. operatively connecting a pair of spaced electrodes to a composite, the composite comprising rutile-phase $TiO_2$ particles and platinum nanoclusters, wherein the composite when exposed to a gas mixture containing carbon monoxide exhibits an electrical resistivity which is proportional to the concentration of carbon monoxide present in the gas mixture;
   b. exposing the composite to a gas mixture containing carbon monoxide; and
   c. measuring the electrical resistance of the composite across the electrodes, while the composite is maintained at a temperature of at least 450° C.

16. The process of claim 15, wherein the gas mixture contains carbon monoxide at concentrations of from about 0-10,000 ppm.

17. The process of claim 15, wherein the gas mixture contains oxygen in concentrations of from about 0.5% to about 21%.

* * * * *